United States Patent [19]

Sved

[11] Patent Number: 5,790,230
[45] Date of Patent: Aug. 4, 1998

[54] COMBINATION EYEGLASS ASSEMBLY OF SPORT OR SAFETY GLASSES WITH DETACHABLE PRESCRIPTION LENSES

[76] Inventor: Robert Sved. 39557 Via Temprano, Murrieta, Calif. 92563

[21] Appl. No.: 602,616

[22] Filed: Feb. 16, 1996

[51] Int. Cl.⁶ .................................. G02C 5/12; G02C 1/02
[52] U.S. Cl. ........................... 351/138; 351/47; 351/57; 351/110
[58] Field of Search ................. 351/41, 44, 47, 351/57, 58, 110, 136, 138, 144, 146, 158; 2/12, 13, 446

[56] References Cited

U.S. PATENT DOCUMENTS

| | | | |
|---|---|---|---|
| 1,923,567 | 8/1933 | Baker | 351/57 |
| 2,501,259 | 3/1950 | Brandt | 88/48 |
| 3,391,976 | 7/1968 | Lindblom | 351/130 |
| 4,500,179 | 2/1985 | Schöhnt | 351/137 |
| 4,556,300 | 12/1985 | Dietrich | 351/137 |
| 4,704,015 | 11/1987 | Grendol et al. | 351/138 |
| 4,806,009 | 2/1989 | Sordillo et al. | 351/88 |
| 5,007,727 | 4/1991 | Kahaney et al. | 351/47 |
| 5,412,438 | 5/1995 | Bollé | 351/138 |

OTHER PUBLICATIONS

*Road Runner Sports,* Spring 1995 Catalog—p. 31.
*Bollé America, Inc.* 1995 Catalog—pp. cover, 3, 24 and 25.

*Primary Examiner*—Huy Mai
*Attorney, Agent, or Firm*—Brown, Martin, Haller & McClain, LLP

[57] ABSTRACT

A combined prescription lens and nose assembly is designed for securing to sport or safety glasses having an integral downwardly facing flange of inverted v-shape, or a separate flange secured to the glasses frame, for extending over a wearer's nose. The assembly includes a flexible nose bridge releasably secured to the flange to engage over a wearer's nose. Separate left and right prescription lenses are separately secured directly to left and right legs of the nose bridge so as to extend closely behind the left and right lens portions of the sunglasses. The lenses are each one piece, frameless members of transparent lens material and the lens material is secured directly to the nose bridge.

27 Claims, 4 Drawing Sheets

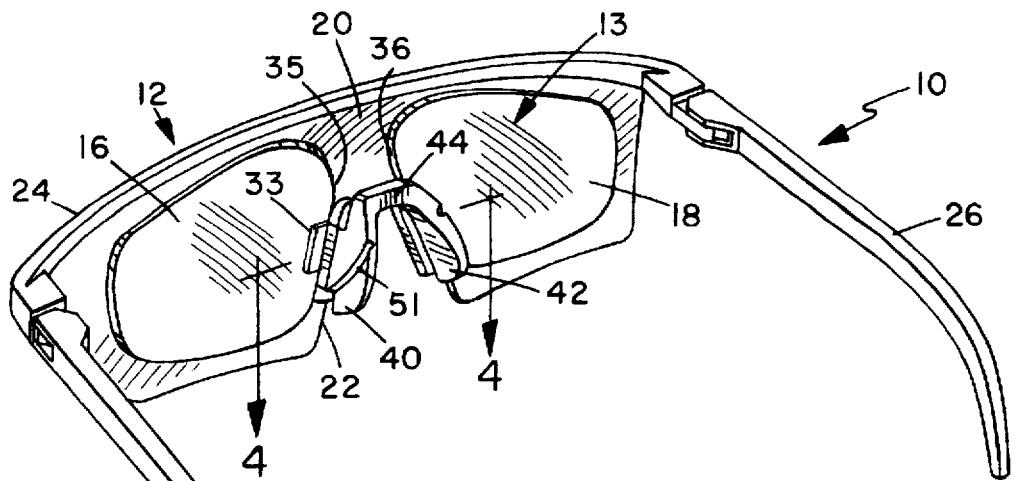
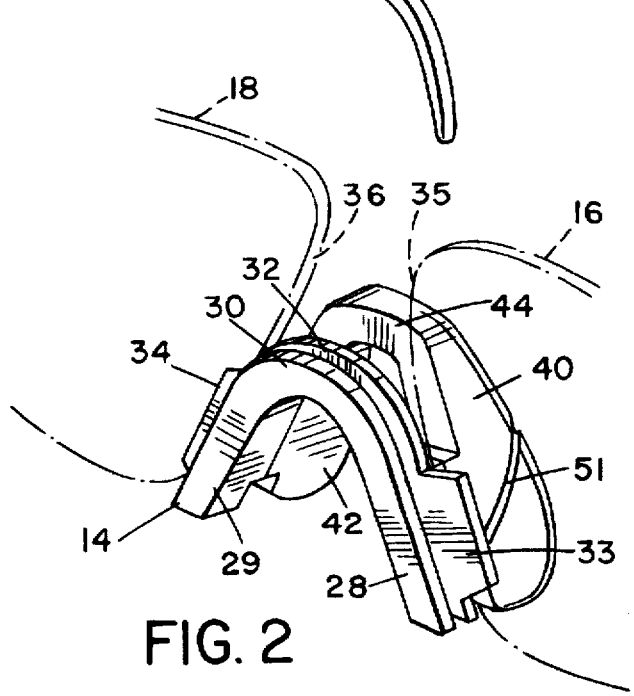
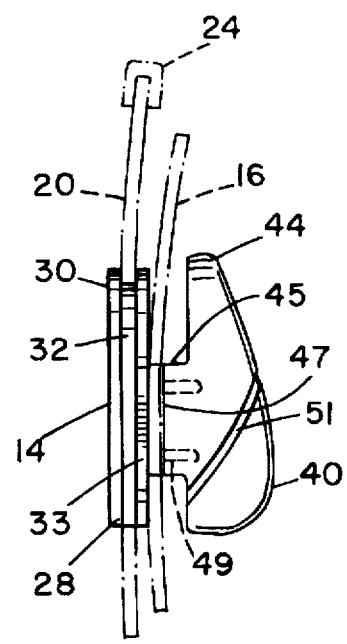
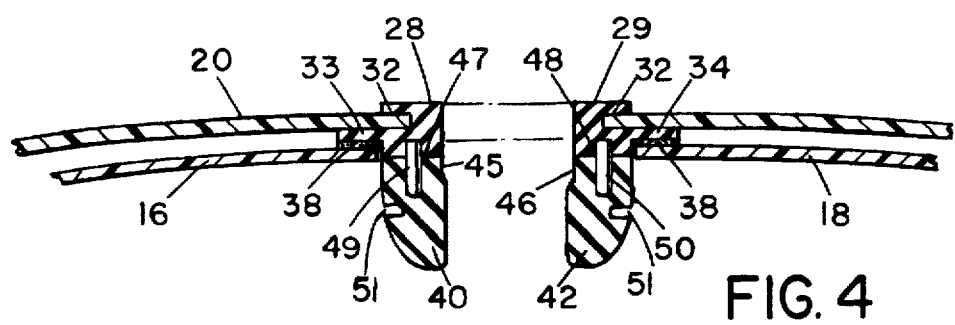
FIG. 1
FIG. 2
FIG. 3
FIG. 4

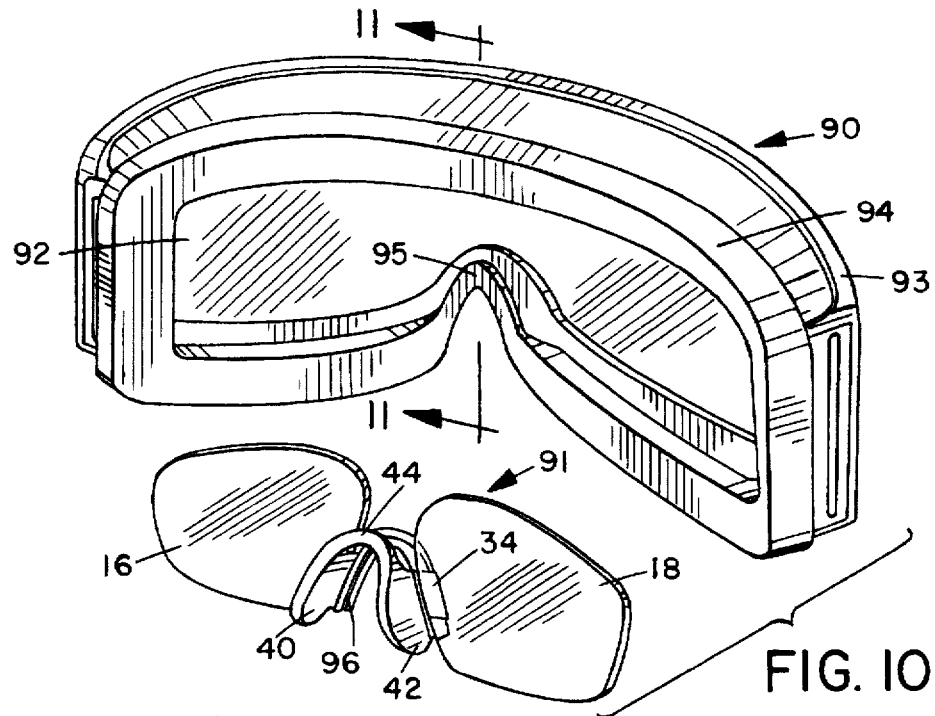
FIG. 10
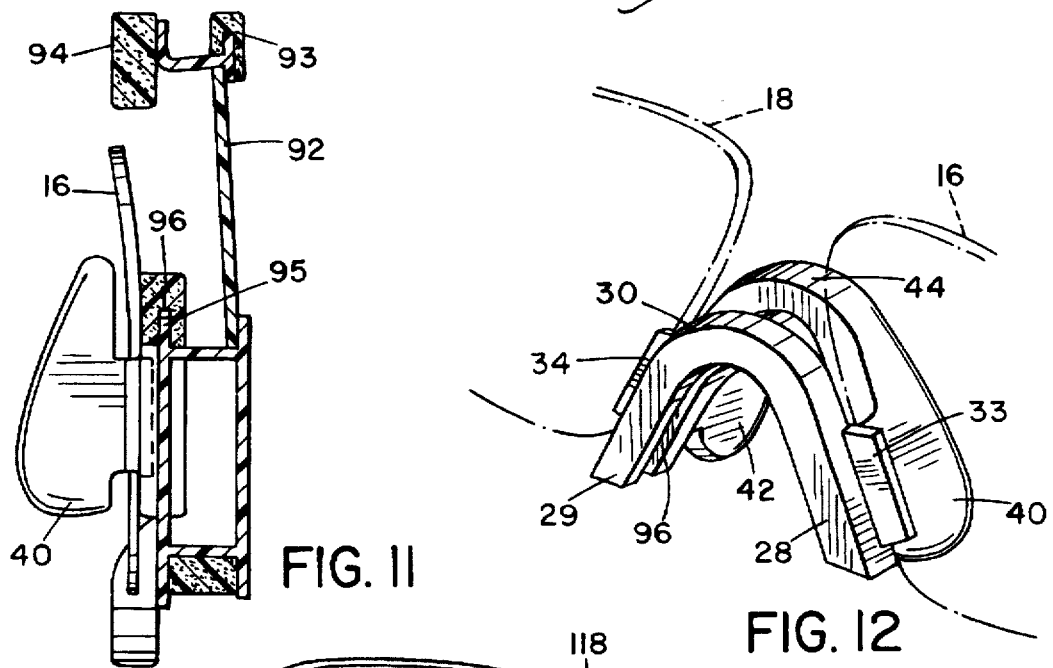
FIG. 11
FIG. 12
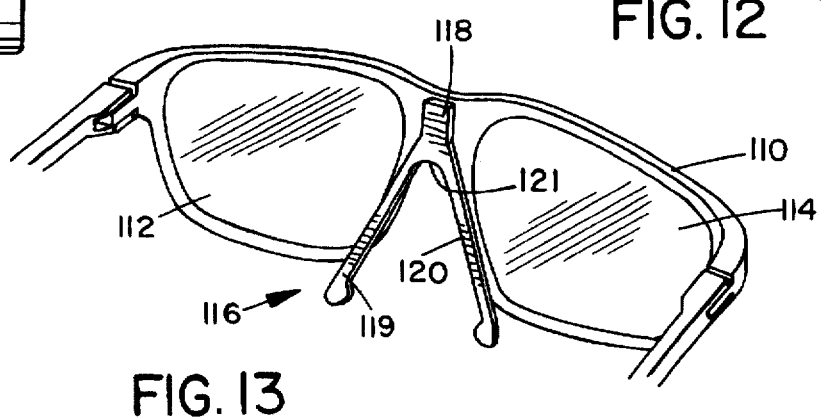
FIG. 13

COMBINATION EYEGLASS ASSEMBLY OF SPORT OR SAFETY GLASSES WITH DETACHABLE PRESCRIPTION LENSES

BACKGROUND OF THE INVENTION

The present invention relates to a combined prescription Rx lens and nosepad assembly for sport and safety glasses.

Over the years a wide variety of sport and safety glasses have been developed to meet specific needs of the wearer. These glasses usually have larger lenses that increase protection and give a larger field of vision compared to standard sunglass frames. These types of sport/safety glasses are usually available in different lens tints and shapes, with most lenses being interchangeable to give the wearer the option of interchanging the lenses to meet specific lighting conditions or activities in which they are involved. Examples would include, but are not limited to, one piece shield lenses with a partial frame or brow bar at the top, two piece shield lenses with a partial frame or brow bar at the top, two piece shield lenses with a partial frame or brow bar at the top, one piece lenses that are rimless, one or two piece lenses with a full frame, goggles and masks.

These types of sport and safety glasses have become very popular. However, with a few exceptions, because of the size or construction of these sport/safety glasses, many styles are not available in prescription. For the person who wears prescription lenses, the choices of sports/safety glasses have been limited and the wearer must purchase separate prescription lenses for each different pair of glasses at considerable expense.

One option for dealing with the problem of providing prescription lenses in one-piece wrap-around lenses is described in U.S. Pat. No. 5,007,727 of Kahaney and Sved. One-piece lens or shield sunglasses are ideal for outdoor activities and sports since they provide protection for the eyes against impact and foreign bodies, they block harmful ultraviolet radiation, and they give the widest field of vision to the wearer. Generally, such sunglasses have an elongate, upper brow bar to which the one piece lens is secured. In the '727 patent, a prescription lens assembly is secured to an elongate plastic member along an upper edge of the assembly, and the plastic member has a downwardly facing groove for mating with the upper edge of a one-piece sunglass lens so that the prescription lenses are nested behind the sunglass lens. However, this has the disadvantage that the prescription lenses must be made larger in order to extend from the brow bar or plastic member down to the lower edge of the sunglass lens, making the assembly heavier and more expensive.

Since the method disclosed in the '727 patent attaches the prescription lenses to a brow bar, it is limited to frame styles that incorporate a brow bar or top rim and cannot be interchanged to rimless or full frame sport/safety glasses and goggles. This method also requires the prescription lens to have the same front surface curvature as the back surface curvature of the brow bar, therefore limiting the power of the prescriptions to be used. Since the prescription lens placement must be at the upper portion of the frame, the prescription lens location cannot be customized if special use, such as golfing, requires the prescription lens location to be lower for optimum use, or in the case where certain bifocal lenses prescribed.

Another method that is commonly used to provide an prescription in sport/safety glasses is to attach a standard full rim frame to the sport/safety frame and insert the prescription lenses in the "second" frame. This method is commonly used in one piece shield style of sport frames as well as ski goggles. Several companies have used this method for attaching prescription lenses including Bolle, Reebock, Adidas and Uvex. Although this method can convert some sport/safety glasses to prescription there are several disadvantages. The full frame provides a rim around the prescription lens that interferes with the visual field, thereby negating much of the benefit of wide field of view provided by shield style glasses or goggles. Another disadvantage is that there is currently no ability to interchange the prescription lenses from one frame style to another, thus requiring the purchase of several pair of prescription lenses at considerable expense. Further, this method limits the prescription lens size, shape and placement, and does not allow customization to meet the specific needs of the wearer, including progressive bifocals. In addition, the "second" full rim frame adds bulk and weight to the sport glass and, further, makes the assembly aesthetically unappealing.

Another method of converting sport/safety frame to prescription eye wear is to cut a hole in the front shield or goggle lens and insert a prescription lens in the hole using a common groove and bevel technique. This technique detracts from the appearance of the glasses/goggles and eliminates versatility for interchanging to different lens tints, shapes or frame styles.

Another problem with sport/safety eye wear is the limitations on properly fitting the glasses to the wearer's nose. Most of the weight of the frame is supported on the nose of the wearer. In the past, nose pieces have been made to one standard shape to fit a hypothetical average person's nose.

Several attempts have been made to design nose pieces to provide the necessary comfort and support to the wearer. Commonly, a strap is extended from one nose pad to the other over the bridge of the nose. Theoretically, this was intended to distribute the weight of the frame more evenly across the wearer's nose. This method has been successful in standard metal eye wear because the pad positions are adjustable by bending the metal post on which they are mounted. In sport/safety frames, however, the fixed bridge portion of the nose piece prevents adjustment of the pads. In many cases, the strap cannot rest on top of the nose and, therefore, does not support any frame weight. A solution, albeit commercially impractical, would be to make a number of different of widths and shapes of nose bridges to properly fit different wearer's noses.

One method used by several companies is to employ pads that rotate on posts on the bridge portion. This allows the angle of the pads to be changed. However, this method does not allow the strap portion of the nose pad to be adjusted to engage the top of the nose.

SUMMARY OF THE INVENTION

It is an object of the present invention to provide a new and improved prescription lens and nosepad assembly for sport and safety glasses or goggles.

According to the present invention, a combined prescription lens and nosepad assembly for a pair of glasses having a central, downwardly facing notch is provided, which comprises a flexible nose bridge for releasable engagement with the notch in the sunglasses, the nose bridge having a left leg, a right leg, and an arched portion connecting the legs for fitting over a wearer's nose, a pair of left and right, rimless and frameless prescription lenses, the left lens being secured to the left leg of the nose bridge and the right lens being secured to the right leg of the nose bridge, and the lenses being positioned rearwardly of the sunglasses when the nose bridge is engaged in the notch.

The lenses may be secured to the legs of the nose bridge in any suitable manner. For example, each lens may be separately bonded with the nose bridge with adhesive, or may be secured to the nose bridge by screw fasteners or the like. By attaching the lenses to the nose bridge, the center of gravity is lowered and the size of the lenses may be reduced. This system allows interchangeability of the lenses from one pair of sunglasses to another. The assembly is particularly suitable for use with sports sunglasses of the type having a single sunglass lens with a brow bar extending across the top of the lens, which already have a central notch over which the nose bridge can engage. This arrangement maintains the original fit of the sport sunglasses without holding the brow bar away from the face. The flexibility of the nose bridge, together with the fact that the prescription lenses are frameless and rimless and separately secured to opposite legs of the nose bridge, permits each lens to be positioned closely behind the appropriate lens region of the sunglasses without holding the sunglasses away from the face. Thus, sunlight will not be let in behind the assembly. The frameless, rimless prescription lenses will allow the original fit of the shield sunglass lens to be maintained.

The nose bridge is preferably of V-shape having a pair of legs connected by a bridge and a groove extending along the legs and bridge for press fitting over the notch in the sunglasses. The same nose bridge and prescription lens assembly may also be secured to glasses having a two piece shield lens, or to safety or sorts goggles by securing a 4-shaped flange member to an upper portion of the glasses or goggles frame such that it depends downwardly in an inverted orientation so as to form a notch over which the nose bridge can be press fit.

Alternatively, the nose engaging portion of the goggles frames may be modified to form a suitable, downwardly facing flange of inverted v-shape, over which the nose bridge can engage.

A flexible nose engaging member having a first nose pad for engaging on one side of a wearer's nose and a second nose pad for engaging on the opposite side of a wearer's nose is preferably secured to the nose bridge for added wearer comfort. The nose pads may be adjustably secured to the nose bridge, for example by means of interengaging slide formations for permitting the nose engaging member to slide up and down relative to the nose bridge in a direction generally along the axis of the respective legs. This permits the nose bridge to be customized to provide a comfortable fit on a particular wearer's nose. As the nose pads slide down relative to the nose bridge, the nose pads will move farther apart, forming a wider nose bridge. Alternatively, by sliding the nose pads upwardly relative to the nose bridge, the nose pads move closer together to form a narrower nose bridge. This avoids the situation where a nose bridge fits poorly so that a gap is left between the bridge of the wearer's nose and the arch or connecting portion of the nose bridge.

The separate, rimless prescription lenses are secured to the nose bridge so that they remain in the same position relative to the sunglass lens or lenses, regardless of adjustment of the nose engaging member. The nose pads may be separate or secured together by means of a flexible strap which will flex as they slide up and down relative to the V-shaped first part of the nose bridge.

The combination prescription lens and nosepad assembly of this invention allows sport or safety glasses to be used together with prescription lenses, without changing the fit of the glasses. The arrangement may be attached to any style of sport or safety glasses, and may be interchanged between different styles and types of glasses. The prescription lens and nosepad assembly is relatively lightweight, and is easy and economical to produce. The assembly may incorporate any size or shape of prescription lens, and allows custom sizing and shaping of prescription lenses using standard techniques. The assembly is attractive and does not detract from the original frame appearance or performance.

The rimless prescription lenses used will provide an uninterrupted field of vision. The adjustable nose pad allows better weight distribution and a more comfortable and stable fit.

BRIEF DESCRIPTION OF THE DRAWINGS

The present invention will be better understood from the following detailed description of some preferred embodiments of the invention, taken in conjunction with the accompanying drawings, in which like reference numerals refer to like parts, and in which:

FIG. 1 is a perspective view from the rear of typical sunglasses with the prescription lens attachment according to a first embodiment of the invention;

FIG. 2 is an enlarged front perspective view of the nose bridge unit;

FIG. 3 is a side elevation view of the nose bridge unit;

FIG. 4 is an enlarged sectional view taken on line 4—4 of FIG. 1;

FIG. 10 is an exploded perspective view from the rear of a pair of sport or safety goggles with a flange for attachment to a prescription lens and nose bridge unit;

FIG. 11 is a section on the lines 11—11 of FIG. 10 with the prescription lens and nose bridge unit engaged over the attachment flange;

FIG. 12 is a perspective view from the rear of the combined prescription lens and nose bridge unit of FIG. 10;

FIG. 13 is perspective view from the rear of a pair of glasses with an attachment piece for releasable connection to the prescription lens and nose bridge unit of FIG. 1;

DESCRIPTION OF THE PREFERRED EMBODIMENT

Figure 5:
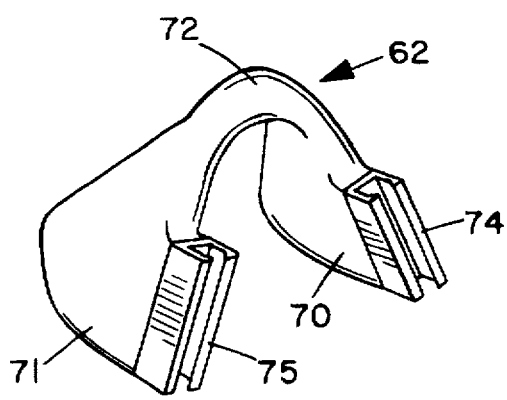
FIG. 5 is a front perspective view of an adjustable nose pad element according to another embodiment of the invention.

FIGS. 1 to 4 illustrate a pair of sport or safety glasses secured to a combined prescription lens and nose bridge assembly, or unit 13, according to a preferred embodiment of the present invention. The assembly comprises a nose bridge 14 releasably secured to the sunglasses 12, and a pair of frameless, rimless, prescription lenses 16,18 secured separately to opposite sides of nose bridge 14.

The sport sunglasses 12 have a one piece, shield style lens 20 with a central notch 22 for fitting over a wearer's nose, a brow bar 24 extending across the top of lens 20, and hinged temples 26 secured to opposite ends of brow bar 24. The notch 22 defines a downwardly facing flange of inverted v-shape. The nose bridge 14 is preferably of resilient plastic material and is generally V or arch-shaped, with opposite left and right legs 28,29 connected by an arch portion 30. An upwardly facing channel 32 extends along the entire length of bridge 14 for releasable press fit engagement over the flange defined by notch 22, as best illustrated in FIG. 4. Each leg 28,29 has an outwardly projecting tab 33,34, respectively, which has a rearwardly facing, generally flat face. This material of which tab 33, 34 is made may be softer and more flexible than the material from which the nose bridge itself is formed to facilitate conforming to the shape of the prescription lens. With such a conformable material, the rearwardly directed face can be flat or curved.

Each prescription lens 16,18 is of a conventional shape for such lenses and is made in one piece from suitable prescription lens material, and has no peripheral frame or rim. Each lens has an inner inclined edge 35,36, respectively, which is at an angle substantially matching that of the respective leg 28,29 of the nose bridge. The outer face of each lens is bonded at edge 35,36 to the respective tab 33,34 with a suitable adhesive material 38. Since the nose bridge is of flexible material, when channel 32 is press fit over notch 22, it will automatically adopt the same contour as notch 22, and the lenses 16 and 18 will be held closely behind the respective left and right portions of lens 20, so that they follow the contour of lens 20, as best illustrated in FIG. 4. By attaching separate, frameless prescription lenses separately to flexible nose bridge, each lens can more readily adopt the same curvature as a one piece sunglass lens, so that the sunglasses can still be mounted close enough to the face to avoid excessive sunlight entering the space behind the glasses. The nose bridge and lenses together form a prescription lens assembly which may be releasably secured to any selected pair of single lens sunglasses, after removing the existing nose bridge.

Preferably, a pair of nose pads 40,42 of softer, cushioning material such as rubber or softer plastic are secured to the nose bridge 14 so as to engage on opposite sides of a wearer's nose for added comfort. The nose pads 40 and 42 may be separate, but in the preferred embodiment they are formed with an integral, interconnecting arch portion 44. Each nose pad 40,42 is a generally rounded, cushion member with a rearwardly facing tab or projection 45,46, respectively, having an inner flat face for engaging the respective leg of the nose bridge. Each leg 28,29 of the nose bridge has a flat outer face 47,48 from which connecting pins 49,50, respectively, project. Pins 49,50 extend into corresponding openings in tabs 45,46 to secure the nose pads to the respective legs, as illustrated in FIGS. 3 and 4. Adhesive may also be used to secure the nose pads to the legs. Preferably, the nose pads 40,42 have inclined, spaced grooves 51 on their outer faces and at least part of their inner faces. The grooves, which are preferably sufficiently deep that only about 1 mm of thickness of a 2–3 mm pad remains, will provide enhanced flexibility. Each nose pad may also have a groove which extends downwardly from approximately half-way down the length of the respective pad, on the outer face of the pad. This groove will act as a hinge to permit the pad to fan out to conform more readily to the contour of a wearer's nose.

Figure 8:
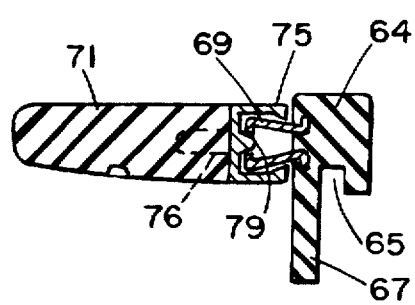
FIG. 8 is an enlarged sectional view taken on line 8—8 of FIG. 7.

The lenses may be secured to the nose bridge by adhesive as illustrated, or may alternatively be secured via screw fasteners or the like extending through aligned openings in the lens and respective tabs 33,34, as illustrated in FIG. 8. In another alternative arrangement, each lens may be provided with a peripheral groove and a monofilament may be extended around the groove and tied with a knot at the respective tab 33 or 34, and then secured to the tab by adhesive or a screw fastener. In each case, the lens is secured directly to the notch in the sunglasses so that it will adopt the same curvature as the sunglasses and extend closely behind the respective lens portion of the sunglasses. The assembly may be readily secured to any selected pair of sunglasses simply by press fitting the nose bridge onto the central notch of the sunglasses. The cushioning nose pads will ensure a comfortable fit over the wearer's nose.

FIGS. 5 to 8 of the drawings illustrate an alternative nose bridge 60 for attaching a pair of separate, rimless prescription lenses as in the previous embodiment to a pair of sport sunglasses 12, and an alternative nose pad member 62 for adjustable attachment to the nose bridge 60. As in the previous embodiment, nose bridge 60 is a generally arch or bridge shaped member of resilient plastic material and has a pair of legs 63,64 connected by an arch portion, with an upwardly facing groove or channel 65 equivalent to channel 32 of the previous embodiment for press fit engagement over a notch 22 in a pair of sport sunglasses. Also as in the previous embodiment, the nose bridge has a pair of tabs 66,67 projecting outwardly adjacent from the lower end of the respective legs 63,64.

In addition to the upwardly facing channel 65, the nose bridge also has a rearwardly facing slide projection 68,69 extending along part of the length of each leg 63,64. The nose pad member 62 has a pair of rounded or bulbous nose pads 70,71 connected by an arch portion 72, as in the previous embodiment, and is made of a cushioning material which is softer than the material of the nose bridge 60. The nose pads are of variable thickness for optimum comfort. Grooves similar to those in the embodiment of FIG. 1–4 may be included in nose pads 70, 71.

Figure 6:
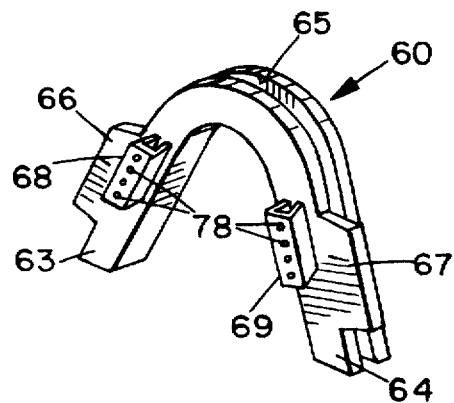
FIG. 6 is a rear perspective view of the matching adjustable nose bridge.
Figure 7:
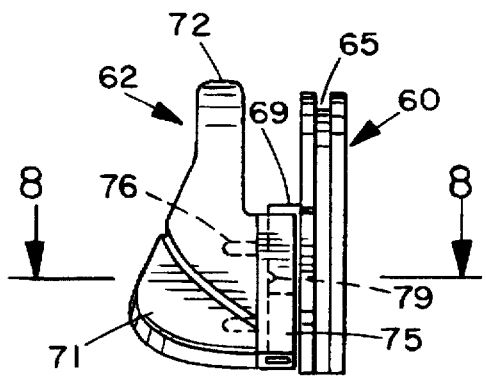
FIG. 7 is a side view of the assembled adjustable unit.

Each nose pad 70,71 has a forwardly facing slide channel 74,75 for releasable sliding engagement over the respective slide projection 68,69 on the nose bridge 60, as best illustrated in FIG. 8, in order to adjust the position of the nose pad along leg 63,64. The channels 74,75 are made separately from the nose pad member and secured to the respective nose pads via pins 76 which are a press fit into aligned holes in the nose pad. As illustrated in FIG. 6, each slide projection 68,69 has an outer flat face having a series of spaced indents or holes 78. Each slide channel 74,75 has an inner flat wall with a single bump or projection 79 for snap engagement in an aligned hole 78, as illustrated in FIG. 8. By moving the nose pads upwardly along legs 63,64, the spacing between the nose pads will be reduced, while movement in the opposite direction will increase the spacing to allow for wearers with wider noses. The locking projection 79 is then simply snapped into an aligned hole to releasably secure the nose pad in a selected position. This arrangement allows the wearer to quickly adjust the width of the nose pads to fit the nose more comfortably.

Figure 9:
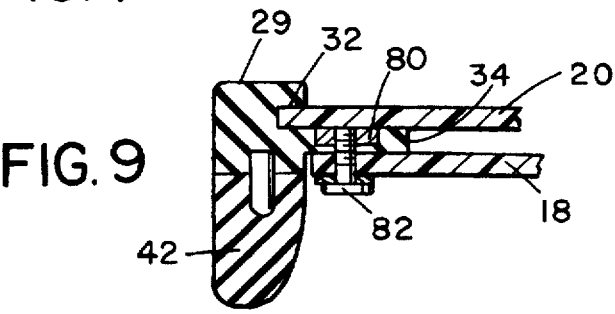
FIG. 9 is a view similar to a portion of FIG. 4, showing a screw attachment for the prescription lens.

As in the previous embodiment, in this embodiment the rimless and frameless prescription lenses will be suitably secured to the projecting tabs, for example by adhesive 38 as in the first embodiment. FIG. 9 illustrates an alternative technique for attaching prescription lens 16 or 18 to a respective tab 33,34. It will be understood that this technique may also be used for attaching the tabs 66,67 of a nose bridge 60 as illustrated in FIGS. 5 to 8 to the respective prescription lens. In this embodiment, the lens 18 and tab 34 have aligned through bores, while tab 34 has a recess aligned for receiving a nut 80, and a threaded bolt 82 extends through the bores in lens 18 and tab 34 for locking engagement in nut 80.

These arrangements allow a wearer requiring prescription lenses to readily wear any selected style of one piece sunglasses or safety glasses without detracting from the appearance or sun shielding operation of the glasses. The existing nose bridge of the glasses is simply removed and replaced with nose bridge 14 or 60, automatically locating the frameless prescription lenses 16 and 18 closely behind the respective eye covering portions of the sunglass lens 20. Although the nose bridge 14, 60 is flexible, allowing it to be attached in different shape notches 22, once attached to the sunglasses via notch 22 the bridge becomes stable, holding lenses 16 and 18 in a relatively stable axial position. The original intended fit of the sunglasses can be maintained with this arrangement, without letting sunlight in at the top, which was a problem with previous combination prescription lens and sunglass assemblies. The prescription lenses can readily be made from plastic or polycarbonate material to any desired prescription depending on the wearer's needs. The prescription may be modified in a known manner to compensate for the distortion produced by the curved shield lenses.

In the above embodiments, the combined prescription lens and nose bridge assembly 13 is secured to a central, downwardly facing notch in a one piece lens, after first removing the existing nose bridge. This is not possible with goggles-type sport or safety glasses, which do not have a removable nose bridge, or with two-piece lenses having a conventional full frame. However, the same nose bridge assembly may still be selectively secured to goggles or sport or safety glasses having two piece lenses, simply by modifying the frame of such glasses to provide an attachment point for a releasable prescription lens and nose bridge unit.

FIGS. 10 to 12 illustrate an alternative embodiment in which a pair of sport or safety goggles 90 is releasably securable to a combined prescription lens and nose bridge unit 91. Goggles 90 have a one piece lens 92 and a peripheral frame 93, and a foam cushion member 94 extending around the inside of frame 93. The nose engaging portion of the inside edge of frame 93 is modified in shape to form an upwardly facing ridge or flange 95 of inverted V-shape.

The combined prescription lens and nose bridge unit 91 is similar to the first embodiment, and like reference numerals have been used for like parts as appropriate. However, rather than an upwardly facing channel 32 as in FIGS. 1 to 4, the arched nose bridge has a downwardly facing channel 96 extending along its entire lower edge, as best illustrated in FIGS. 11 and 12. Channel 96 is shaped and dimensioned for press fit engagement over the ridge or flange 95 formed on the goggles frame 93, as illustrated in FIG. 11.

Figure 18:
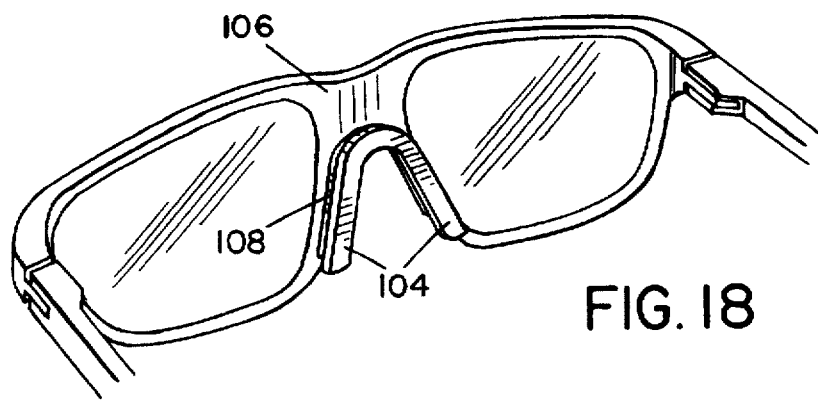
FIG. 18 is a perspective view from the rear of a pair of glasses with an attachment piece for releasable connection to the prescription lens and nose bridge unit of FIG. 1.

When the channel 96 of the nose bridge is press fit over ridge or flange 95, the frameless prescription lenses 16 and 18 will be appropriately positioned behind the left and right eye portions, respectively, of the one piece lens 92. The lens may be a safety lens for use by workers in hazardous environments, or may be of sunglass material to provide goggles for wearing in sporting activities, such as skiing. This permits a wearer requiring prescription lenses to utilize such goggles by simply attaching a unit 91. Alternatively, a continuous downward facing flange 104, such as that shown in FIG. 18, can be molded into the arched nose bridge of the goggle, or, as shown, in the nose bridge 108 of sunglass frame 106. Flange 104 will mate with channel 32 of bridge section 14 which supports prescription lenses 16, 18.

FIG. 13 illustrates another alternative attachment mechanism which enables a combined prescription lens and nose bridge unit 13 as illustrated in FIGS. 1 to 4 to be attached to a conventional glasses frame 110 for holding two separate safety or sunglass lenses 112,114. The attachment mechanism comprises a flat, Y-shaped member 116 having a straight leg 118 which is suitably secured in any suitable manner to a central portion of frame 110 so that the flared arms 119,120 depend downwardly to form an inverted V-shaped notch 121 equivalent to notch 22 of the first embodiment. The upwardly facing groove or channel 32 of the nose bridge in the first embodiment can be press fit over notch 121 in an equivalent manner to the first embodiment, positioning the prescription lenses 16 and 18 behind the left lens 112 and right lens 114, respectively. Thus, the same prescription lens and nose bridge unit may be readily secured to a pair of sunglasses having separate left and right lenses, as well as to one piece shield sunglasses or to safety glasses or goggles. The Y-shaped member 116 may alternatively be used with the goggles style glasses of FIGS. 10 to 12, securing straight leg 118 to an upper portion of the goggles frame at an appropriate position.

Figure 14:
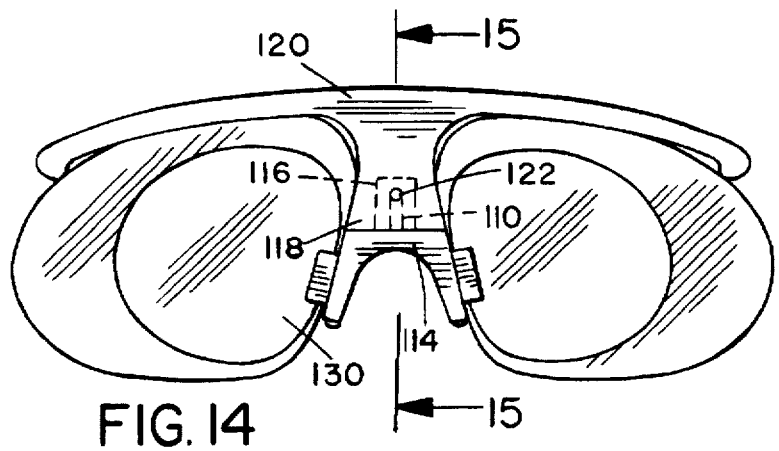
FIG. 14 is a rear view of an alternate embodiment of the invention using a tab and notch attachment means.
Figure 15:
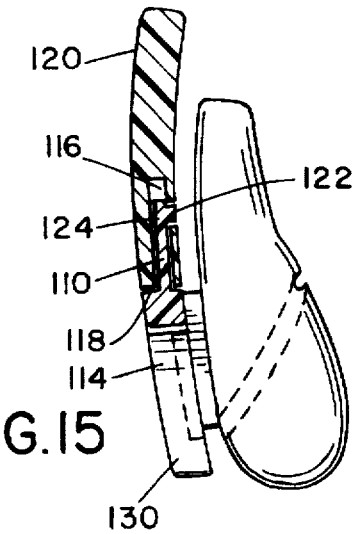
FIG. 15 is a cross-sectional view taken along line 15—15 of FIG. 14.
Figure 16:
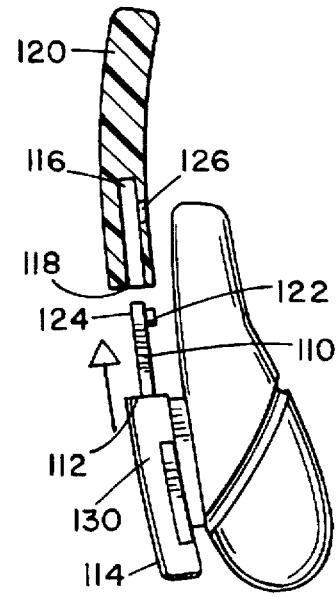
FIG. 16 is a side view showing the prescription lens unit separated from the glasses' frames.

FIGS. 14–16 illustrate yet another means for releasably attaching the prescription lens unit to different types of glasses. In this embodiment a tab 110 extends upward from the upper portion 112 of nose bridge 114. Resilient tab 110 mates with a notch 116 in the lower edge 118 of frame 120. Tab 110 has a resilient button 122 near its upper end 124 which compresses sufficiently to slides within notch 116. When the button 122 and opening 126 are aligned, button 122 resiles to fit within opening 126, locking the tab 110 into notch 116. To remove the prescription lens unit 130 from the frames, button 122 is pressed back into opening 126 while pulling downward on the prescription lens unit 130 to slide the tab 110 out of notch 116.

Figure 17:
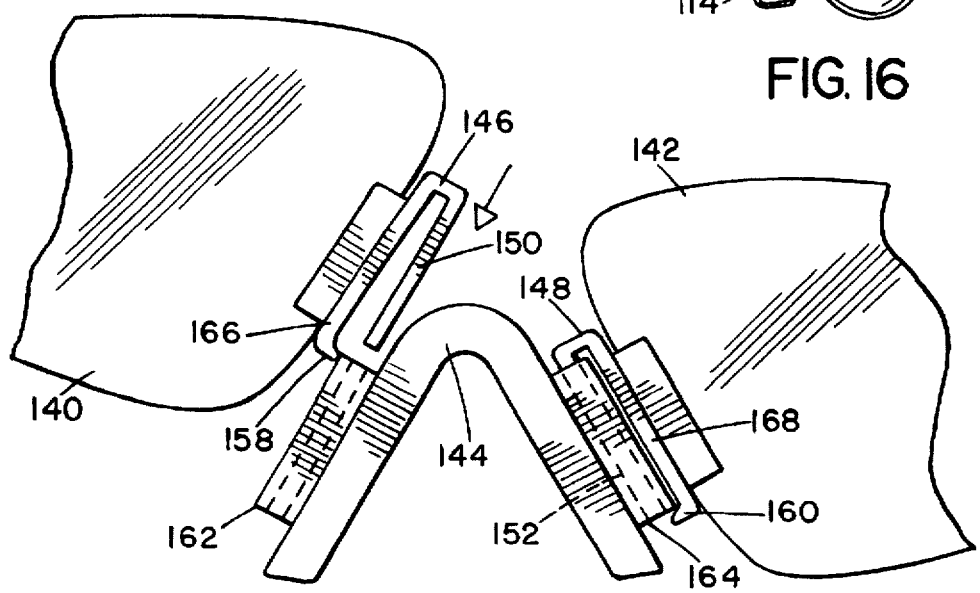
FIG. 17 is a rear view of a clip attachment means.

In FIG. 17, an alternate means for releasably locking the prescription lens 140, 142 into the nose bridge 144 is provided by clips 146, 148. Arms 150, 152 interfit with sleeves 154, 156. Once inserted into the sleeves 154, 156, teeth 158, 160 on outer arms 166, 168 slip under the sleeve, lower ends 162, 164 to lock the lenses in place. To remove the prescription lens, teeth 158, 160 are pulled away from the respective sleeves and the arms 150, 152 can be slid upward and out of the sleeves 154, 156.

This invention permits the same combined nose bridge and prescription lens unit to be used with different types and styles of sunglasses, sports glasses or safety glasses, including goggles. The unit is relatively lightweight and inexpensive, and avoids the need for purchasing several sets of prescription glasses for various purposes. The unit will not detract from the original styling or fit of the glasses to which it is attached. The use of rimless prescription glasses ensures that the unit does not interrupt the field of vision any further than the glasses to which the unit is attached.

Although some preferred embodiments of the invention have been described above by way of example only, it will be understood by those skilled in the field that modifications may be made to the disclosed embodiments without departing from the scope of the invention, which is defined by the appended claims.

I claim:

1. A combination prescription lens and sunglasses or goggle assembly, comprising:
    a pair of sunglasses or goggles having a central, downwardly facing notch for engagement over a wearer's nose, the sunglasses or goggles having left and right lens portions for extending over the left and right eyes, respectively, of a wearer;
    a detachable nose bridge of resilient material for releasable engagement in the notch, the nose bridge having a left leg, a right leg, and an arched portion connecting the legs for fitting over a wearer's nose; and
    a pair of left and right eye prescription lenses separately secured to the left and right leg, respectively, of the nose bridge in a position spaced rearwardly of the left and right lens portions, respectively;
    each prescription lens comprising a one-piece member of transparent lens material having a frameless peripheral edge, each lens having an inner portion directly secured to the nose bridge and the remainder of the peripheral edge being free and unobscured.

2. The assembly as claimed in claim 1, wherein each lens is bonded to the nose bridge.

3. The assembly as claimed in claim 1, including a fastener screw securing each lens to the respective leg of the nose bridge.

4. The assembly as claimed in claim 1, including left and right nose pads of softer material than the nose bridge for fitting on opposite sides of a wearer's nose, the left leg and nose pad having first interengageable securing means for securing the left nose pad to the left leg and the right leg and nose pad having second interengageable securing means for securing the right nose pad to the right leg of the bridge.

5. The assembly as claimed in claim 4, including an integral arch portion connecting the left and right nose pads.

6. The assembly as claimed in claim 4, wherein each nose pad has an outer surface and a series of spaced grooves extending across at least part of the outer surface of each nose pad.

7. The assembly as claimed in claim 4, wherein each nose pad has at least one groove, said groove comprising hinge means for flexing said nose pad to conform to a wearer's nose.

8. The assembly as claimed in claim 4, wherein said interengageable securing means each comprise interengageable first and second parts, one of said parts comprising an elongate channel and the other part comprising a tongue for releasable sliding engagement in said channel to adjust the position of the respective nose pad on the respective leg of the nose bridge.

9. The assembly as claimed in claim 8, wherein each leg of said nose bridge has a rearwardly facing tongue extending along at least part of its length, and each nose pad has an open ended channel for sliding engagement over the respective channel.

10. The assembly as claimed in claim 1, wherein each leg of said nose bridge has an outwardly projecting tab having a rearwardly facing generally flat face, and each lens is bonded directly to the face of the respective tab so as to be positioned closely behind the respective sunglass portion.

11. The assembly as claimed in claim 1, wherein the nose bridge is of resilient plastic.

12. The assembly as claimed in claim 11, including a pair of left and right nose pads of resilient material which is softer than the nose bridge material, and securing means for securing the respective left and right nose pads to the left and right legs, respectively, of the nose bridge.

13. The assembly claimed in claim 1 further comprising attachment means for releasably attaching said detachable nose bridge to said sunglasses or goggles.

14. The assembly claimed in claim 13 wherein said attachment means comprises an interfitting flange and channel combination.

15. The assembly claimed in claim 13 wherein said attachment means comprises a tab and notch combination.

16. The assembly claimed in claim 13 wherein said attachment means comprises a clip and sleeve combination.

17. An eyeglass assembly, comprising:
    a pair of glasses having left and right lens portions for extending over the left and right eyes, respectively, of a wearer, a frame secured to said lens portions, and a central, downwardly facing flange of inverted V-shape for extending over a wearer's nose;
    a V-shaped nose bridge of resilient material, the flange and nose bridge having interengageable securing means for releasable, press fit engagement of said nose bridge on said flange, the nose bridge having a left leg, a right leg, and an arched portion connecting the legs;
    a pair of left and right eye prescription lenses separately secured to the left leg and right leg, respectively, of the nose bridge in a position spaced rearwardly of the left and right lens portions, respectively; and
    each prescription lens comprising a one-piece member of transparent lens material having a frameless, transparent peripheral edge, each lens having an inner portion directly secured to the nose bridge and the entire peripheral edge of each lens apart from said inner portion being frameless when assembled in said eyeglass assembly.

18. The assembly as claimed in claim 17, wherein the glasses have a one-piece lens including said left and right lens portions and a central portion connecting said left and right lens portions, the lens having an upper edge and a lower edge, said frame comprising a brow bar extending across the upper edge of said lens only and said lower edge being frameless, and said flange comprising a downwardly facing, central notch in said central portion of said one-piece lens.

19. The assembly as claimed in claim 17, wherein said frame comprises a full frame surrounding the periphery of said right and left lens portions, said frame having an upper portion and a lower portion, and said downwardly facing flange being secured to said frame at a central location spaced behind said right and left lens portions.

20. The assembly as claimed in claim 19, wherein said downwardly facing flange includes a stem projecting from a central portion of said flange and secured to said upper portion of said frame.

21. A combined prescription lens and nose bridge assembly, comprising:
    a V-shaped nose bridge of resilient material having a left leg, a right leg, an arched portion connecting the legs, and releasable connecting means for releasably connecting the bridge to a V-shaped flange on a pair of glasses;
    a pair of left and right eye prescription lenses separately secured to the left and right leg, respectively, of the nose bridge for positioning rearwardly of left and right lens portions, respectively, of said pair of glasses; and
    each prescription lens comprising a one-piece member of transparent lens material having a frameless, transparent peripheral edge, each lens having an inner portion directly secured to the nose bridge, and the entire peripheral edge of each lens outside said secured inner portion being free and frameless when assembled in said eyeglass assembly.

22. An interchangeable eyeglass assembly, comprising:

a first pair of glasses having left and right lens portions for extending over the left and right eyes, respectively, of a wearer, and a frame secured to said lens portions;

a V-shaped nose bridge of resilient material having a left leg, a right leg, an arched portion connecting the legs, and a first interengageable formation for releasably securing the nose bridge to the first pair of glasses;

the first pair of glasses having a second interengageable formation for releasable mating engagement with said first interengageable formation when said nose bridge is secured to the pair of glasses; and a pair of left and right eye prescription lenses secured to the left and right leg, respectively, of the nose bridge for positioning said prescription lenses in a location spaced rearwardly of the left and right lens portions, respectively, of the first pair of glasses to which the nose bridge is secured.

23. The assembly as claimed in claim 22, wherein the first pair of glasses are sunglasses.

24. The assembly as claimed in claim 22, wherein the first interengageable formation comprises a V-shaped flange and the nose bridge has a channel for press fit engagement over said flange, said channel comprising said second interengageable formation.

25. The assembled as claimed in claim 24, wherein said first pair of glasses comprise sport sunglasses having a single lens including said left and right lens portions, said frame comprising a brow bar secured to said lens, and said lens having a downwardly facing central notch comprising said V-shaped flange.

26. The assembly as claimed in claim 22, wherein said first and second interengageable formations comprise an interfitting flange and channel combination.

27. The assembly as claimed in claim 22, wherein said first and second interengageable formations comprise a notch and a tab for releasable snap engagement in said notch.

* * * * *